United States Patent
Takatsuka et al.

(10) Patent No.: US 6,497,858 B1
(45) Date of Patent: Dec. 24, 2002

(54) METHOD OF REMINERALIZING TEETH

(75) Inventors: Tsutomu Takatsuka, Osaka; Naomi Yasuda, Ibaraki; Kazushi Ebisudani, Osaka, all of (JP)

(73) Assignee: Sunstar Kabushiki Kaisha, Osaka (JP)

( * ) Notice: Subject to any disclaimer, the term of this patent is extended or adjusted under 35 U.S.C. 154(b) by 0 days.

(21) Appl. No.: 09/381,902

(22) PCT Filed: Mar. 25, 1997

(86) PCT No.: PCT/JP97/00987

§ 371 (c)(1),
(2), (4) Date: Oct. 28, 1999

(87) PCT Pub. No.: WO98/42297

PCT Pub. Date: Oct. 1, 1998

(51) Int. Cl.[7] ............................ A61K 7/16; A61K 7/18; A61K 7/22

(52) U.S. Cl. ............................ 424/49; 424/52; 424/54; 424/57

(58) Field of Search ............................ 424/54, 52, 49, 424/57

(56) References Cited

U.S. PATENT DOCUMENTS 4,923,683 A * 5/1990 Sakuma et al. ............... 424/52
5,858,333 A * 1/1999 Winston et al. ............... 424/57

FOREIGN PATENT DOCUMENTS

| GB | 2 206 338 | 1/1989 |
| JP | 05-065211 | 3/1993 |
| JP | 05-339136 | 12/1993 |
| WO | 94/04460 | 3/1994 |

* cited by examiner

*Primary Examiner*—Shep K. Rose
*Assistant Examiner*—Donna Jagoe
(74) *Attorney, Agent, or Firm*—Foley & Lardner

(57) ABSTRACT

A method of remineralizing teeth by using an oral hygiene composition comprising a polyvinyl acetal diethylaminoacetate and a fluoride ion-feeding compound; and the composition for use in the method.

11 Claims, No Drawings

METHOD OF REMINERALIZING TEETH

FIELD OF THE INVENTION

The present invention relates to an oral composition effective for remineralizing teeth, and a method for using the same.

BACKGROUND OF THE INVENTION

In an oral cavity, there is an equilibrium state in which a constituent ingredient of teeth, hydroxy apatite, dissolves from the teeth, and a calcium ion or a phosphate ion in a saliva deposits onto the tooth surface. Due to this equilibrium state, the tooth surface is always changing. When the equilibrium moves towards the dissolution of hydroxy apatite, a white spot develops on the tooth surface, which leads to a caries-inducing state referred to as demineralization. When the equilibrium moves towards the reformation of a demineralized enamel from hydroxy apatite, which is referred to as remineralization, caries can be prevented or treated by the remineralization.

A major factor governing the equilibrium is a saturation degree of hydroxy apatite in the oral cavity. That is, when hydroxy apatite becomes supersaturated, the remineralization occurs. Reversely, when the saturation degree of hydroxy apatite is lowered, the demineralization occurs. Since hydroxy apatite dissolves in an acid, in an acidic region, the saturation degree is lowered and the demineralization occurs.

Thus, there has been proposed an oral composition into which hydroxy apatite and calcium compounds, constituent ingredients thereof are blended and which promotes the remineralization.

For example, there is described that the remineralization is promoted by using certain hydroxy apatite in JP-A 55-57514, tetra-calcium phosphate in JP-A 1-71807, or amorphous calcium phosphate in U.S. Pat. No. 5,562,895. There is described a composition with added soluble calcium phosphate containing calcium and phosphate in the ionized state in JP-A 8-319224, and there is described a toothpaste containing silica and dicalcium phosphate in JP-A 8-502988 (WO 94/10969).

For the remineralization, it is also known that fluoride ion-feeding compounds release a fluoride ion to promote a remineralization process and, thereby, reduce caries that has previously been existed within a tooth structure. For example, there are proposed a combination of xylitol and a fluoride in U.S. Pat. No. 371,145, and a combination of hydroxy apatite and a fluoride in JP-A 1-110608. However, although a certain effect has been recognized for the primary teeth, a product which can be said to be sufficient for remineralizing the second teeth has not been developed yet.

By the way, it has been hitherto known that a fluoride ion reinforces a dentine. Thus, an attempt to enhance the caries preventing effect has been tried by intensifying such an action of a fluoride ion. In JP-A 63-246316, pyridoxine derivatives are blended into an oral composition for the purpose of promoting uptake of a fluoride ion and improving an acid-resistant property of the teeth. There is proposed a poly-cationic polymer in JP-A 3-5417. However, none of them disclose the remineralizing action.

The previous methods, which employ a composition into which hydroxy apatite is blended or an oral composition into which a fluoride is blended, can not accomplish the desired effect on the teeth under an oral cavity environment where the teeth are easily demineralized, or on the teeth which has already begun to be demineralized. Also, there is a limitation that a pH of a formulation as an oral composition is required to adjust to a higher pH than that of a weak acid because when the oral cavity is made acidic, the demineralization is caused.

An object of the present invention is to enhance the effects of preventing or treating caries of an enamel or root surface, or dentin hyperesthesia, by promoting the ability of fluorine to remineralize.

SUMMARY OF THE INVENTION

The present inventors extensively studied the promotion of the remineralizing action of a fluoride ion and, as a result, found that polyvinyl acetal diethylaminoacetate has an excellent remineralizing action promoting effect. Polyvinyl acetal diethylaminoacetate was developed as a coating agent for tablets, and, for instance, there is reported in JP-A 5-339136 that it is effective for suppressing dental plaque accumulation or promoting adsorption of a fluoride onto the tooth surface. However, its remineralizing action promoting effect is not known.

Also, the present inventors found that even when a pH of an oral composition is adjusted to an acidic region of about 3–6.5, the demineralization is not caused, and, unexpectedly, the remineralizing action promoting effect is remarkably improved than in a neutral region. Moreover, the present inventors found that the remineralizing action promoting effect is also improved by blending an anionic surfactant therein.

The present invention was completed based on such novel findings and in one aspect thereof, provides a method of remineralizing teeth which comprises using an oral composition comprising polyvinyl acetal diethylaminoacetate and a fluoride ion-feeding compound which feeds a fluoride ion. This oral composition may further contain an anionic surfactant.

In an another aspect, the present invention provides an oral composition for remineralizing the teeth, which is used for the method of the present invention.

DETAILED DESCRIPTION OF THE PREFERRED EMBODIMENTS

Polyvinyl acetal diethylaminoacetate to be used in the present invention is an acetal produced by dehydration between polyvinyl alcohol and acetaldehyde, and which is a basic high-molecular compound in which a part of the remaining hydroxyl groups are bound to diethylaminoacetic acid via an ester linkage and, for example, a commercially available product such as "AEA" (Sankyo Corporation) may be used.

An amount of polyvinyl acetal diethylaminoacetate to be blended is in the range of 0.01–10% by weight, preferably in the range of 0.02–2% by weight, from a viewpoint of the promotion of the remineralizing action.

As the fluoride ion-feeding compound which feeds a fluoride ion, there are sodium fluoride, potassium fluoride, ammonium fluoride, calcium fluoride, copper fluoride, zinc fluoride, lithium fluoride, cesium fluoride, zirconium fluoride, tin fluoride, sodium monofluorophosphate, potassium monofluoro-phosphate, sodium titanium fluoride, potassium titanium fluoride, hexylamine hydrofluoride, laurylamine hydrofluoride, cetylamine hydrofluoride, lysine hydrofluoride, glycine hydrofluoride, alanine hydrofluoride, fluorosilane and the like, and they can be used alone or in a combination of two or more of them. In view of the oral use, preferred are sodium fluoride, potassium fluoride, ammonium fluoride, tin fluoride, sodium monofluorophosphate, and potassium monofluorophosphate. An amount of the fluoride ion-feeding compound to be blended is in the range of 10–50,000 ppm, preferably 90–20,000 ppm in terms of a fluoride ion based on the total amount of the oral composition, from a viewpoint of the remineralizing effect. When the amount is below 10 ppm, the remineralizing action can not be expected and, when it exceeds 50,000 ppm, the remineralization promoting effect by polyvinyl acetal diethylaminoacetate does not increase much, being not economical. In a method of using almost every day for a long period of time, the concentration in the composition of 90–5,000 ppm is particularly preferred and, in a method of using at long-term intervals exceeding one month, 9,000–20,000 ppm is particularly preferred.

As the anionic surfactant to be used in the present invention, there are salts of N-long chain acyl basic amino acid such as sodium salt of N-acyl-L-glutamate, sodium salt of N-hydrogenated tallow fatty acid acyl-L-glutamate, sodium lauroyl sarcosinate, water-soluble salts of higher alkyl sulfate having alkyl group of 8–18 carbon atoms such as sodium lauryl sulfate and sodium myristyl sulfate, polyoxyethylene alkyl sulfate salt, alkylsulfoacetate salt, α-olefin sulfonate salt, sulfosuccinate derivatives, sodium salt of higher fatty acid monoglyceride monosulfate, N-methyl-N-palmitoyltauride salts and the like. An amount of the anionic surfactant to be blended is 0.01–10% by weight, preferably 0.1–5% by weight based on the total amount of the oral composition.

As an acid to be used for adjusting a pH of the oral composition, citric acid, malic acid, phosphoric acid, and aromatic carboxylic acids such as benzoic acid, nicotinic acid and salicylic acid, and salts thereof are exemplified, and one or more selected from them may be used. A preferred pH range is 3–6.5. When a pH is below 3, the demineralization by an acid is remarkable and, when a pH exceeds 6.5, the effect becomes weak. An amount of the acid to be blended is preferably 0.01–3% by weight and, when it exceeds 3% by weight, a physical property as an oral composition becomes unstable.

The oral composition of the present invention may be appropriately formulated, depending upon its use, into a form such as toothpaste, pasta, powder or liquid dentifrice, wetting dentifrice, gel, cream, mouthwash, spray, foam, coating agent and the like, according to the conventional methods. Other ingredients to be blended are not particularly limited and the known polishing agents, humectants, thickening agents, foaming agents, preservatives, flavoring agents, therapeutic agents and the like may be blended into the oral composition, so long as they do not deteriorate the effects of the present invention.

A container may be made of compatible materials, all kinds of dispenser-container are usable, and a laminate tube made of aluminium or plastics, a plastic container such as of squeeze-type and pump dispenser, or an aerosol container may be used. In the case of a gel or varnish form, the composition may be contained in a syringe.

The method of the present invention may be practiced by applying the oral composition to the demineralized portion of the tooth such as by brushing or mouth washing. For example, in the case of a dentifrice or a mouthwash, they are used one to three times a day according to the conventional using method. Usually, 0.2–1.5 g of a dentifrice or 5–20 ml of a mouthwash as a daily amount is used so that the daily amount of a fluoride is 0.1–2 mg, particularly preferably approximately 1 mg. Moreover, the oral composition of the present invention may be formulated into the form such as a gel or a varnish to specifically apply onto the demineralized portion of the teeth in a topical manner. In the case of a gel or a varnish for the topical application, it may be applied in the frequency of once a month to once a year.

The remineralization of teeth is accomplished by the above way of using and, thereby, the effects of preventing or treating caries, root surface caries and dentin hyperesthesia can be exerted.

Next, the present invention will be further illustrated by way of the following Experimental Examples and Examples, which are not to be constructed to limit the scope of the present invention. Unless otherwise indicated, "%" represents percent (%) by weight.

EXPERIMENTAL EXAMPLE 1

An artificial caries was produced using a procedure described by D. J. White et al., *Caries Research*, Volume 22, page 27 (1988) and tested for the remineralization promoting effect in vitro. Namely, a tooth was demineralized to its sub-surface area with a demineralizing solution containing 50% saturated hydroxy apatite/0.1 M of lactic acid/pH 5.0 to produce the artificial caries. The tooth was immersed in a treatment solution each time for one minute, four times a day, by simulating a conventional method for use of a dentifrice or a mouthwash. The tooth was demineralized with an acid for at least three hours a day, and was immersed in an artificial saliva for the remaining time. The treatment was repeated for eight days. Then, the tooth was cut into thin sections and the X-ray photograph of the sections was taken to calculate its mineral amount. The remineralization ratio was calculated as a ratio of the increased mineral amount relative to the demineralized mineral amount. A greater value shows the greater remineralization. The results are shown in Table 1.

TABLE 1

| | Treatment solution | pH | Remineralization ratio |
|---|---|---|---|
| Comparative Example 1 | Citrate buffer (0.1 M) | 6.5 | 0 |
| Comparative Example 2 | Polyvinyl acetal diethylaminoacetate (0.1%) + Citrate buffer (0.1 M) | 6.5 | 0 |
| Comparative Example 3 | Sodium fluoride (0.05%) + Phosphate buffer (0.1 M) | 8 | 31 |
| Comparative Example 4 | Sodium fluoride (0.05%) + Phosphate buffer (0.1 M) | 6.5 | 30 |
| Comparative Example 5 | Sodium fluoride (0.05%) + Citrate buffer (0.1 M) | 3 | 15 |
| Example 1 | Sodium fluoride (0.05%) + Polyvinyl acetal diethylaminoacetate (0.1%) + Phosphate buffer (0.1 M) | 6.5 | 54 |
| Example 2 | Sodium fluoride (0.05%) + Polyvinyl acetal diethylaminoacetate (0.1%) + Citrate buffer (0.1 M) | 5 | 66 |
| Example 3 | Sodium fluoride (0.05%) + Polyvinyl acetal diethylaminoacetate (0.1%) + Phosphate buffer (0.1 M) | 3 | 69 |
| Example 4 | Sodium fluoride (0.05%) + Polyvinyl acetal diethylaminoacetate (0.1%) + Sodium lauryl sulfate (0.1%) | 6.5 | 69 |

TABLE 1-continued

| | Treatment solution | pH | Remineralization ratio |
|---|---|---|---|
| Example 5 | Sodium fluoride (0.05%) + Polyvinyl acetal diethylaminoacetate (0.1%) + Sodium salt of N-acyl-L-glutamic acid (0.1%) | 6.5 | 68 |
| Example 6 | Sodium fluoride (0.05%) + Polyvinyl acetal diethylaminoacetate (0.1%) + Sodium lauroyl sarcosinate (0.1%) | 6.5 | 63 |

These results show that, in the method of the present invention, the remineralization is caused more remarkably by adding sodium fluoride together with polyvinyl acetal diethylaminoacetate than by adding sodium fluoride alone. Moreover, the results show that the remineralization is caused even in an acidic region where the demineralization is usually caused and, additionally, show that the significantly excellent remineralization is accomplished by adding an anionic surfactant thereto.

EXAMPLES 7–11

A toothpaste was prepared according to the formulation in Table 2 using the conventional procedures.

TABLE 2

| | Amount (%) | | | | | |
|---|---|---|---|---|---|---|
| | Comparative Example | Example | | | | |
| Ingredient | 7 | 7 | 8 | 9 | 10 | 11 |
| Sodium fluoride | 0.2 | 0.2 | 0.2 | 0.2 | 0.2 | 0.2 |
| Polyvinyl acetal diethylaminoacetate | — | 0.1 | 0.1 | 0.1 | 0.1 | 0.1 |
| Polyoxyethylene hydrogenated castor oil | — | 1.0 | — | — | — | 0.5 |
| Sodium lauryl sulfate | 1.0 | — | — | — | 1.0 | 0.5 |
| Sodium lauroyl sarcosinate | — | — | — | 1.0 | — | — |
| Sucrose fatty acid ester | — | — | 1.0 | — | — | — |
| Citric acid | — | 0.5 | — | — | — | 0.2 |
| Sodium dihydrogenphosphate | — | — | 0.5 | — | — | 0.2 |
| Silicic acid anhydride | 20 | 20 | 20 | 20 | 20 | 20 |
| Sodium carboxymethyl cellulose | 1.5 | 1.5 | 1.5 | 1.5 | 1.5 | 1.5 |
| Saccharin sodium | 0.2 | 0.2 | 0.2 | 0.2 | 0.2 | 0.2 |
| Sorbitol | 60 | 60 | 60 | 60 | 60 | 60 |
| Titanium oxide | 0.3 | 0.3 | 0.3 | 0.3 | 0.3 | 0.3 |
| Flavor | 0.7 | 0.7 | 0.7 | 0.7 | 0.7 | 0.7 |
| Water | balance | balance | balance | balance | balance | balance |
| pH | 6.5 | 6.5 | 6.0 | 5.5 | 5.0 | 5.0 |

EXPERIMENTAL EXAMPLE 2

The dentifrice compositions of Examples 7–11 were tested in vivo according to the Rat Caries Assay described by R. Schmidt et al., *Journal Clinical Dentistry*, Volume 1, page 75 (1989). CARA rats were used in the test. The rats were fed with a caries-inducing food (56% sucrose, 28% skim milk) beginning on the day 25 after birth, and *Streptococcus sorbinus* and *Actinomyces viscosus* were administered twice a day on the days 25 and 26 after birth. Each 0.1 ml of dentifrices of Comparative Examples or Examples was applied once a day for twenty-one days, and the number of initial smooth surface caries was evaluated after the completion of the test. The results of the assay are shown in Table 3.

TABLE 3

| | Average/rat | |
|---|---|---|
| | N | Number of initial caries |
| Comparative Example 7 | 10 | 11.2 |
| Example 7 | 10 | 1.7 |
| Example 8 | 10 | 1.5 |
| Example 9 | 10 | 2.0 |
| Example 10 | 10 | 2.2 |
| Example 11 | 10 | 1.9 |

These results show that the development of initial caries was more remarkably suppressed by administrating a dentifrice to which sodium fluoride together with polyvinyl acetal diethylaminoacetate is added than a dentifrice to which sodium fluoride alone is added. This effect is due to the promotion of the remineralizing ability.

EXPERIMENTAL EXAMPLE 3

A clinical test was performed as essentially described by Stephen et al., *International Dental Journal*, Volume 44, page 287 (1994). Namely, a clinical test for human was performed on 11–12 years old children for one year. The children were directed and managed to, two to three times according to the conventional method, take approximately 1 g of a test dentifrice on a toothbrush, brush the oral cavity for a few minutes and, thereafter, rinse the mouth. At the starting and ending points of the test, inspects were performed to record the number of the tooth surface with a white spot and caries tooth surface, and the increased number relative to that at the starting point of the clinical test was calculated. The results of the clinical test are shown in Table 4.

TABLE 4

| | N | Increased number of the white spot or caries tooth surface |
|---|---|---|
| Comparative Example 7 | 512 | 3.5 |
| Example 7 | 459 | 1.9 |
| Example 10 | 507 | 2.2 |

These results show that the method of the present invention suppressed the increase of the number of the white spot on the tooth surface produced by the demineralization, and at the same time suppressed the increase of the tooth surface caries, which was accompanied by the promotion of the remineralizing ability.

EXAMPLE 12

A toothpaste was prepared according to the following formulation using the conventional procedures.

| Ingredient | Amount (%) |
|---|---|
| Sorbitol | 61.5 |
| Xylitol | 9.0 |
| Silicic acid anhydride | 12.0 |
| Carboxymethyl cellulose | 0.5 |
| Sodium polyacrylate | 0.6 |
| Sodium lauryl sulfate | 1.1 |
| Polyoxyethylene hydrogenated castor oil | 0.5 |
| Polyvinyl acetal diethylaminoacetate | 0.1 |
| Citric acid | 1.5 |
| Titanium oxide | 6.5 |
| Flavor | 0.7 |
| Sodium fluoride | 0.32 |
| Purified water | balance |

A pH was adjusted to 6.0.

Approximately 0.5 g of the present composition was applied three times a day to a child developing a white spot on the tooth surface to clean the oral for six months. The composition had an excellent remineralization promoting ability and, after one year, no caries developed from the white spot was recognized.

EXAMPLE 13

A mouthwash was prepared according to the following formulation using the conventional procedures.

| Ingredient | Amount (%) |
|---|---|
| Glycerol | 35.5 |
| Propylene glycol | 5.0 |
| Sodium polyacrylate | 3.0 |
| Polysorbate | 0.5 |
| Sodium lauroyl sarcosinate | 0.5 |
| Saccharin sodium | 0.1 |
| Polyvinyl acetal diethylaminoacetate | 0.1 |
| Malic acid | 0.2 |
| Flavor | 0.1 |
| Sodium fluoride | 0.05 |
| Purified water | balance |

A pH was adjusted to 6.0.

A child at high risk of the development of caries was rinsed in the oral cavity with approximately 20 ml of the present composition, which was then disgorged. This treatment was performed, after cleaning the oral cavity, three times a day for one year. The composition of the present invention had an excellent remineralization promoting ability and could prevent the development of caries.

EXAMPLE 14

A mouthwash was prepared according to the following formulation using the conventional procedures.

| Ingredient | Amount (%) |
|---|---|
| Glycerol | 10.5 |
| Sodium lauryl sulfate | 0.2 |
| Polyoxyethylene hydrogenated castor oil | 1.0 |
| Polyvinyl acetal diethylaminoacetate | 0.1 |
| Phosphoric acid | 0.1 |
| Flavor | 0.1 |
| Ethanol | 8.0 |
| Sodium fluoride | 0.05 |
| Xylitol | 10.0 |
| Purified water | balance |

A pH was adjusted to 5.5.

A person whose gingiva had retracted and whose dental root had been exposed was rinsed in the oral cavity with approximately 10 ml of the present composition, which was then disgorged. This treatment was performed, after normally cleaning the cavity, three times a day for six months. The present composition had an excellent remineralization promoting ability and root surface caries and dentin hyperesthesia were not produced.

EXAMPLE 15

A gel was prepared according to the following formulation using the conventional procedures.

| Ingredient | Amount (%) |
|---|---|
| Glycerol | 30.5 |
| Saccharin sodium | 0.1 |
| Polyvinyl acetal diethylaminoacetate | 0.2 |
| Phosphoric acid | 0.1 |
| Flavor | 0.1 |
| Sodium fluoride | 1.1 |
| Purified water | balance |

A pH was adjusted to 4.0.

The gel was applied once a month to a part of the tooth surface developing a white spot using a syringe. After six months, no development of caries from the white spot was recognized.

EXAMPLE 16

A fluorine varnish for topical application was prepared according to the following formulation using the conventional procedures.

| Ingredient | Amount (%) |
|---|---|
| Ethanol | 60.0 |
| Rosin | 20.0 |
| Polyvinyl acetal diethylaminoacetate | 1.0 |

-continued

| Ingredient | Amount (%) |
|---|---|
| Phosphoric acid | 0.3 |
| Sodium fluoride | 2.2 |
| Purified water | balance |

A pH was adjusted to approximately 5.0.

The varnish was applied to a part of the tooth surface developing a white spot once per two months using a syringe. After one year, the white spot was not enlarged and the varnish had an excellent remineralization promoting ability.

As stated above, according to the present invention, a method which promotes the remineralization of teeth and has the excellent effects of preventing or treating caries or hyperesthesia is provided, by using an oral composition obtained by blending polyvinyl acetal diethylaminoacetate or an anionic surfactant therein, further by adjusting a pH of the oral composition to 3–6.5.

What is claimed is:

1. A method of remineralizing teeth which comprises using an oral composition comprising polyvinyl acetal diethylaminoacetate that is blended with a fluoride ion-feeding compound which feeds a fluoride ion.

2. The method according to claim 1, wherein the oral composition to be used comprises an anionic surfactant.

3. The method according to claim 1, wherein the pH of the oral composition is 3–6.5.

4. The method according to claim 1, wherein the fluoride ion-feeding compound is sodium fluoride.

5. A method of remineralizing teeth which comprises using an oral composition comprising 0.01–10% by weight of polyvinyl acetal diethylaminoacetate and a fluoride ion-feeding compound which feeds a fluoride ion.

6. The method according to claim 5, wherein the pH of the oral composition is 3–6.5.

7. The method according to claim 5, wherein the fluoride ion-feeding compound is sodium fluoride.

8. A method of remineralizing teeth which comprises using an oral composition comprising 0.01–10% by weight of polyvinyl acetal diethylaminoacetate that is blended with a fluoride ion-feeding compound which feeds a fluoride ion.

9. The method according to claim 8, wherein the oral composition comprises an anionic surfactant.

10. The method according to claim 8, wherein the pH of the oral composition is 3–6.5.

11. The method according to claim 8, wherein the fluoride ion-feeding compound is sodium fluoride.

* * * * *